United States Patent [19]

Payne et al.

[11] Patent Number: 4,830,858

[45] Date of Patent: May 16, 1989

[54] SPRAY-DRYING METHOD FOR PREPARING LIPOSOMES AND PRODUCTS PRODUCED THEREBY

[75] Inventors: Nicholas I. Payne; J. Roger Salmon, both of Wirral, United Kingdom

[73] Assignee: E. R. Squibb & Sons, Inc., Princeton, N.J.

[21] Appl. No.: 699,981

[22] Filed: Feb. 11, 1985

[51] Int. Cl.$^4$ .................. A61K 37/22; A01N 25/26; A61J 5/00; B32B 9/02

[52] U.S. Cl. .................................. 424/450; 264/4.1; 264/4.3; 264/4.6; 428/402.2; 424/417

[58] Field of Search .................. 264/4.1, 4.3, 4.6; 428/402.2; 424/38, 417, 450

[56] References Cited

U.S. PATENT DOCUMENTS

| | | | |
|---|---|---|---|
| 4,229,360 | 10/1980 | Schneider et al. | 424/36 |
| 4,247,411 | 1/1981 | Vanlerberghe et al. | 424/36 |
| 4,311,712 | 1/1982 | Evans et al. | 514/773 |
| 4,485,054 | 11/1984 | Mezel et al. | 424/38 |
| 4,508,703 | 4/1985 | Redziniak et al. | 514/78 |

FOREIGN PATENT DOCUMENTS 0023302 2/1981 European Pat. Off. ............. 264/4.1

OTHER PUBLICATIONS

Ryman, B. E., "The Use of Liposomes as Carriers of Drugs and Other Cell-Modifying Molecules," Proc. 6th Int'l Congr. Pharmacol. 5, 91, (1976) published in Drug Applications, *Clinical Pharmacology*, vol. 5, pp. 91–103, Pergamon Press (1975).

*Primary Examiner*—Douglas W. Robinson
*Assistant Examiner*—J. Kilcoyne
*Attorney, Agent, or Firm*—Burton Rodney

[57] ABSTRACT

A method is provided for preparing a stable liposome precursor in the form of a mixture of spray-dried liposomal components including one or more biologically active compounds which may be stored dry and reconstituted with water to form a liposomal preparation immediately prior to use. The dry liposome precursor is also provided.

28 Claims, No Drawings

SPRAY-DRYING METHOD FOR PREPARING LIPOSOMES AND PRODUCTS PRODUCED THEREBY

FIELD OF THE INVENTION

The present invention relates to a method for preparing stable liposome precursors in the form of mixtures of spray-dried liposomal components, which may or may not include a carrier material, which liposome precursors are employed to form liposome preparations, and to intermediates and products produced in such method.

BACKGROUND OF THE INVENTION

Liposomes are widely described in the literature and their structure is well known. They are formed by amphipathic molecules such as the class II polar lipids, that is, phosphatidyl cholines, ethanolamines and serines, sphingomyelins, cardiolipins, plasmalogens, phosphatidic acids and cerebrosides. Liposomes are formed when phospholipids or other suitable amphipathic molecules are allowed to swell in water or aqueous solutions to form liquid crystals usually of multilayer structure comprised of many bilayers separated from each other by aqueous material. Another type of liposome is known consisting of a single bilayer encapsulating aqueous material which may also be referred to as a unilamellar vesicle. "If water-soluble materials are included in the aqueous phase during the swelling of the lipids they become entrapped between the lipid bilayers. Alternatively, lipid soluble materials may be dissolved in the lipid and, hence, may be incorporated into the lipid bilayers themselves," Ryman, B. E., "The Use of Liposomes as Carriers of Drugs and Other Cell-Modifying Molecules," Proc. 6th Int'l. Congr. Pharmacol. 5, 91 (1976), published in "Drug Applications," *Clinical Pharmacology*, vol. 5, pp. 91-103, Pergamon Press (1975).

In recent years there has been much interest in the use of liposomes as carriers of compounds which are of interest because of one or other biological property, for example, medicaments, proteins, enzymes, hormones and diagnostic agents, hereinafter referred to as "biologically active compounds." Liposomes have been suggested as carriers for drugs, see Ryman, supra at page 91 and Gregoriadis, G., "Enzyme or Drug Entrapment in Liposomes: Possible Biomedical Application," *Insolubilized Enzymes*, Ed. M. Salmona et al., Raven Press, N.T. 1974, pp. 165-177.

Water-soluble materials are encapsulated in the aqueous spaces between the biomolecular layers. Lipid soluble materials are incorporated into the lipid layers although polar head groups may protrude from the layer into the aqueous space. The encppsulation of these compounds can be achieved by a number of methods. The method most commonly used involves casting a thin film of phospholipid onto the wall of a flask by evaporation of an organic solvent. When this film is dispersed in a suitable aqueous medium, multilamellar liposomes are formed (also referred to as coarse liposomes). Upon suitable sonication, the coarse liposomes form smaller similarly closed vesicles.

Water-soluble biologically active compounds are usually incorporated by dispersing the cast film with an aqueous solution of the compound. The unencapsulated compound is then removed by centrifugation, chromatography, dialysation or some other suitable procedure. Lipid-soluble biologically active compounds are usually incorporated by dissolving them in the organic solvent with the phospholipid prior to casting the film. Providing the solubility of these compounds in the lipid phase is not exceeded or the amount present is not in excess of that which can be bound to the lipid, liposomes prepared by the above method usually contain most of the compound bound in the lipid bilayers; separation of the liposomes from unencapsulated material is not required. Other methods of preparing liposomes have been described although these are mainly specialized methods producing unilamellar liposomes and include reverse-phase evaporation of an organic solvent from a water-in-oil emulsion of phospholipid, infusion of organic solutions of phospholipid into large volumes of aqueous phase and detergent removal from mixed micelles of detergent and lipid.

Aqueous liposome dispersions only have limited physical stability. The liposomes can aggregate and precipitate as sediment. Although this sediment may be redispersed, the size distribution may be different from that of the original dispersion. This may be overcome to some extent by incorporation of caarged lipids into the liposomes. In addition, on storage the biologically active compounds may be lost into the external aqueous phase which restricts the potential of these preparations as practical dosage forms. This is particularly notable for low molecular weight water-soluble compounds but lipid soluble compounds too can partition into the external aqueous medium. If the volume of the aqueous medium is large, this loss can be significant. In addition, depending upon the type of lipid and biologically active compound present in the liposome, there is the potential for chemical degradation of the lipid components and-/or the biologically active components in the aqueous dispersion.

These factors restrict the use of liposomes as practical carriers of biologically active compounds. One solution suggested for overcoming the limited physical stability of liposomes is to prepare and store the lipid/biologically active compound film and then disperse the film to form liposomes just prior to administration. However, unit dose film preparation presents serious practical difficulties in that the containers would require a high surface area to facilitate solvent evaporation and deposition of a thin film suitable for rapid rehydration to form liposomes readily. This type of container by virtue of its bulk would present severe storage problems. Other methods suggested for preparing liposome components in a solid form for storage have included freeze-drying the prepared aqueous liposome suspension as described in U.S. Pat. Nos. 4,229,360 and 4,247,411 and by freeze-drying the liposome components from a suitable organic solvent as described in U.S. Pat. No. 4,311,712. These freeze-dried preparations result in a porous matrix of liposome components which is easily hydrated.

BRIEF DESCRIPTION OF THE INVENTION

In accordance with the present invention, a method is provided for preparing a spray-dried mixture of liposomal components, which mixture is not subject to the physical stability problems set out above, and which may be employed to form liposome preparations immediately prior to administration. The method of the present invention includes the steps of forming a solution of at least one liposome-forming amphipathic lipid, optionally, at least one biologically active compound, optionally, at least one adjuvant, and optionally a suitable water-soluble particulate carrier material, and spray-drying the above solution (or solution/suspension) to form a dry mixture of liposomal components.

The spray-drying technique may be carried out employing conventional spray-drying equipment such as a Büchi Minispray Model B190.

In addition, in accordance with the present invention, a method is provided for forming a liposome preparation which method includes the step of exposing the spray-dried mixture of liposome components to water thereby causing the liposomal components to hydrate and the carrier material (where present) to dissolve to give a liposome preparation similar to that prepared by hydration of cast films with a solution of the carrier material.

Further, in accordance with the present invention, there is provided the intermediate formed above which is comprised of the relatively stable particulate spray-dried mixture of liposomal components and water-soluble carrier (where present) which is useful for forming the liposome preparation.

The problems associated with the physical stability of liposome dispersions on storage may be overcome by forming the aqueous dispersion of the spray-dried liposomal components and carrier material (where present) prior to administration. Additionally, the chemical integrity of the biologically active compounds and lipid components may be protected in the spray-dried powdered preparations by the incorporation of antioxidants therein or packing the powdered material under inert atmospheres, for example.

DETAILED DESCRIPTION OF THE INVENTION

In carrying out the method of the invention for preparing the particulate liposomal components and optionally water-soluble carrier materials, at least one liposome forming amphipathic lipid, optionally, at least one biologically active compound, and, optionally, at least one adjuvant are dissolved in a solvent and this solution by itself or together with a solution or suspension of water-soluble physiologically acceptable carrier material is spray-dried. In an optional embodiment, the solution of the lipid, biologically active compound and adjuvant may be formed by dissolving the biologically active compound and adjuvant in the lipid.

The lipid will be present in the solution (optionally containing a second solvent), in an amount of within the range of from about 1 to about 25% by weight, depending upon the solubility of the lipid in the solvent or solvent mixture used, and preferably from about 2.5 to about 12.5% by weight of such solution. The optional biologically active compound and optional adjuvant material will be present in the solution to be spray-dried in varying amounts depending upon the nature of the particular compound and/or material employed.

The ratio of lipid to optional biologically active compound in the solution to be spray-dried will depend upon the lipid solubility or binding of the biologically active compound used. Thus, the solution to be spray-dried will normally contain a weight ratio of lipid:optional biologically active compound of within the range of from about 5:1 to about 1000:1 and preferably from about 10:1 to about 200:1 depending upon the particular biologically active compound to be employed. For example, where the biologically active compound is an anti-infective, such as an antibiotic or an anti-fungal agent, the lipid will be present in a weight ratio to the biologically active compound of within the range of from about 5:1 to about 1000:1 and preferably from about 10:1 to about 300:1. Where the biologically active compound is a contrast agent, the lipid will be present in a weight ratio to the contrast agent in an amount of within the range of from about 5:1 to about 1000:1 and preferably from about 10:1 to about 200:1.

The amounts of optional adjuvant material and biologically active material employed in the coating will comprise amounts conventionally employed in forming liposomes.

The amounts of liposomal components to be mixed with a solution of the carrier material will depend upon physical characteristics of the carrier material such as surface area and isotonicity requirements. Thus, the solution to be spray-dried will normally contain a weight ratio of liposomal components to carrier material in an amount of within the range of from about 0.03:1 to about 5.0:1 and preferably from about 0.05:1 to about 3.0:1.

Any amphipathic lipid which is known to be suitable for preparing liposomes by known methods can be used in the method of this invention. Thus, a wide variety of lipids may be used but non-immunogenic and biodegradable lipids would be preferred. Examples of suitable lipids are the phospholipids, for example, natural lecithins, such as egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline, with egg lecithin or soya bean lecithin being preferred.

The biologically active compound employed in the present invention may be any compound of biological interest; for example, the compound may be a medicament, such as an anti-infective, for example, amphotericin B, ketoconazole, isoconazole, miconazole and benzyl penicillin, anti-tumor agents, such as 5-fluorouracil, methotrexate, actinomycin D, enzyme, hormone, contrast agent, marker compound or NMR imaging agent, such as 4-succinyl-4-amino-2,2,6,6-tetramethylpiperidine-1-oxyl.

Examples of contrast agents suitable for use in the present invention include, but are not limited to the following: N,N'-bis[2-hydroxy-1-(hydroxymethyl)ethyl]-5-[(2-hydroxy-1-oxopropyl)amino]-2,4,6-triiodo-1,3-benzenedicarboxamide (Bracco 15,000), metrizamide, diatrizoic acid, sodium diatrizoate, meglumine diatrizoate, acetrizoic acid and its soluble cationic salts, diprotrizoic acid and its soluble inorganic and organic cationic salts, iodamide, sodium iodipamide, meglumine iodipamide, iodohippuric acid and its soluble salts, iodomethamic acid and its soluble salts, iodopyracetiodo-2-pyridone-N-acetic acid and its soluble salts, 3,5-diiodo-4-pyridone- N-acetic acid (iodopyracet), 3,5-diiodo-4-pyri- done-N-acetic acid diethanolamine salt, iodo-2- pyridone-N-acetic acid and its amine salt, iothalamic acid and its soluble salts, methanesulfonic acid, metrizoic acid and its soluble salts, sodium ipodate, ethiodized oil, iopanoic acid, iocetamic acid, tyropanoate sodium, iopydol, iophenoxic acid, iophendylate, and other chemically related iodinated contrast agents. Unless indicated otherwise, where applicable, the contrast agents which may be employed herein include inorganic, organic and cationic salts of the above contrast agent, such as the potassium salt, calcium salt, lithium salt, arginin salt, cystein salt, glycin salt, glycyl glycin salt, N-methyl glucosamine salt and other non-toxic aliphatic and alicyclic amines employed in preparing water soluble salts. Other X-ray contrast agents which may be employed herein are disclosed in German Offenlegungsschrift DT 2935-195.

The final liposome preparation containing a contrast agent prepared by the method of the invention may be employed as described in U. S. Pat. No. 4,192,859 which is incorporated herein by reference.

Other proteins and drugs available for use herein as optional biologically active compounds include steroids such as hydrocortisone, colchicine, insulin, cyclic AMP and α-thiodeoxyguanosine, chelating agents and cell modifying substances, such as antigens and interferon inducers.

The present invention is particularly useful in the case of lipid-soluble or lipid-bound biologically active compounds (which include some water-soluble compounds, such as proteins).

The method of this invention, like other methods of preparing liposomes, will result in partial incorporation of water-soluble biologically active compounds. Usually the formation of liposomes containing this type of compound is followed by removal of the unencapsulated material; however, in some instances coadministration of unencapsulated and liposomally entrapped biologically-active compounds may be advantageous.

The optional adjuvants suitable for use in the present invention may be:

(a) substances which are known to provide a negative charge on the liposomes, for example, egg phosphatidic acid or dicetyl phosphate;

(b) substances known to provide a positive charge, for example, stearyl amine, or stearyl amine acetate;

(c) substances shown to affect the physical properties of the liposomes in a more desirable way; for example, sterols such as cholesterol ergosterol, phytosterol, sitosterol, 7-dehydrocholesterol or lanosterol will affect membrane rigidity;

(d) substances known to have antioxidant properties toiimprove the chemical stability of the particulate carrier coated with liposome components, such as tocopherol, propyl gallate, ascorbyl palmitate, or butylated hydroxy toluene.

Suitable solvents for use in dissolving or aiding in dissolution of the above-mentioned mixture of lipid and optional biologically active compound and optional adjuvant include, but are not limited to, ethanol, methanol, chloroform, dichloromethane, diethyl ether, carbon tetrachloride, ethyl acetate, dioxane, cyclohexane and the like, with methanol, ethanol or chloroform being preferred.

The carrier material which may be present may be any physiologically acceptable free-flowing powder which, even after processing, will remain substantially granular and free-flowing. The carrier material will have a high water-solubility, for example, in excess of about 10% by weight in water and a rapid dissolution rate in water, for example, complete solution in 3 to 4 minutes at 40° C., and should be suitable for intravenous use. In addition, a suitable carrier material will be substantially insoluble in the solvent used for dissolving the mixture of lipid, optional active compound and optional adjuvant and will form an isotonic solution in water in a concentration range of from about 0.5 to about 10% w/v, and preferably from about 0.9 to about 7% w/v. Examples of suitable carrier materials include sorbitol, mannitol, sodium chloride, xylitol, or naturally occurring amino acids such as arginine or glycine, with sorbitol being preferred.

It may be advantageous to use micronized forms of the carrier materials (that is, having an average particle size of less than about 10 microns) as the high surface area would facilitate the hydration and dissolution of the liposomal components. However, the carrier materials may have an average particle size of up to 500 microns and still be useful. The amount of carrier material used may be adjusted so that the final reconstituted suspension is iso-osmotic with the blood, although for small volume injections this may not be necessary. As a suitable aqueous medium for dispersion distilled water, isotonic saline or buffer solution may be used, the temperature of which may be modified to exceed the phase transition temperature of the lipid components used in formulation.

The liposomal components (excluding the biologically active compound) preferably are binary mixtures of lecithin and a sterol selected from the group listed hereinabove, or ternary mixtures of lecithin, dicetyl phosphate, and a sterol selected from the group listed hereinabove, in the preferred molar ratios of 7:2:1, respectively. The molar percentage of lecithin may range from about 55 to about 95% and the sterol from about 5 to about 35% based on a binary mixture. The molar percentage of lecithin may range from about 50% to about 80%, the dicetyl phosphate from 0 to about 30%, and the sterol from about 5 to about 30%, base on a ternary lipid mixture. Lecithin is employed to take advantage of its property of swelling in salt solutions to form liposomes. Dicetyl phosphate has the property of imparting a negative charge to the lipid membranes.

The components which constitute the liposomal mixture are commercially available or may readily be prepared.

The spray-drying step may be carried out employing an average temperature of from about 5 to about 60° C. including an average air inlet temperature of within the range of from about 20 to about 60° C., an average air outlet temperature of within the range of from about 5 to about 40° C. and employing an average air throughput of within the range of from about 300 to about 700 liters per hour. However, the final conditions will depend upon the nature of the liposomal components and the solvent(s) employed By suitable containment and sterilization of component materials, a dry sterile mixture of carrier material together with the liposomal components is produced. The dry sterile mixture of the invention may be packed in sterile unit dose vials under aseptic conditions and reconstituted immediately prior to use by the physician.

The final liposome formulations prepared as described above may be administered parenterally, for example, intravenously, as well as orally and topically.

The following Examples represent preferred embodiments of the present invention.

EXAMPLE 1

Twenty-five grams (25 g) sorbitol were dissolved in distilled water (50 ml) and added to 750 ml methanol containing egg lecithin((6.05 g), ergosterol (0.25 g) and amphotericin B (0.25 g). The solution was spray-dried in a Büchi Minispray Model B190 (inlet temperature =27° C.; outlet temperature =20° C.; air throughput =500 liter/hour).

The resultant powder may be packaged and stored in sterile unit dose vials under aseptic conditions and reconstituted immediately prior to use.

Sterile, pyrogen free water (10 ml) was added to a portion of the above product (0.631 g) in a vial and agitated by hand to form a liposomal preparation.

EXAMPLE 2

Twenty-five grams (25 g) sorbitol were dissolved in distilled water (50 ml) and added to 750 ml methanol containing dimyristoylphosphatidylcholine (4.235 g), dimyristoylphosphatidylglycerol (1.815 g) and amphotericin B (0.378 g). The solution was spray-dried in a Buchi Minispray Model B190 (inlet temperature =27° C.; outlet temperature =20° C.; air throughput =500 liters/hour).

The resultant powder may be packaged and stored in sterile unit dose vials under aseptic conditions and reconstituted immediately prior to use.

Sterile pyrogen-free water (10 ml; at 37° C.) was added to a portion of the above product (0.629 g) in a vial and agitated by hand to form a liposomal preparation.

EXAMPLE 3

Egg lecitiin (6.05 g), ergosterol (0.25 g) and amphotericin B (0.25 g) were dissolved in methanol (750 ml) and spray-dried in a Buchi Minispray Model B190 (inlet temperature =47° C.; outlet temperature =30° C.; air throughput =500 liters/hour).

The resultant powder may be packaged and stored in sterile unit dose vials under aseptic conditions and reconstituted immediately prior to use.

Sterile, pyrogen-free saline (0.9% w/v) (10 ml) was added to a portion of the above product (0.131 g) in a vial and agitated by hand to form a liposomal preparation.

EXAMPLE 4

Dimyristoylphosphatidylcholine (4.235 g), dimyristoylphosphatidylglycerol (1.815 g) and amphotericin B (0.378 g) were dissolved in methanol (750 ml) and spray-dried in a Büchi Minispray Model B190 (inlet temperature =47° C.; outlet temperature =30° C.; air throughput =500 liters/hour).

The resultant powder may be packaged and stored in sterile unit dose vials under aseptic conditions and reconstituted immediately prior to use.

Sterile, pyrogen-free saline 0.9% w/v (10 ml) (at 37° C.) was added to a portion of the above product (0.129 g) in a vial and agitated by hand to form a liposomal preparation.

What is claimed is:

1. A method for preparing a spray-dried mixture of liposomal components which may be stored dry and reconstituted to form a liposome, which comprises forming a solution of lipsomal components in a suitable organic solvent comprised of from about 1 to about 25% by weight of at least one liposome-forming lipid, optionally, at least one biologically active compound, and, optionally, at least one adjuvant which imparts advantageous properties to the final liposome, and adding an aqueous solution or suspension of at least one water-soluble, physiologically acceptable carrier material which is suitable for intravenous injection but which is substantially insoluble in said organic solvent, the weight ratio of liposomal components to carrier material being within the range of from about 0.03:1 to about 5:1, and spray-drying the so-formed mixture to form a dry mixture of liposomal components.

2. The method as defined in claim 1 wherein the solution is formed by dissolving said lipid, said biologically active compound and, optionally, said adjuvant in one or more organic solvents.

3. The methodaas defined in claim 1, wherein the solution is formed by dissolving the optional biologically active compound and optional adjuvant in said lipid.

4. The method as defined in claim 1 wherein said carrier material has a water-solubility in excess of 10% by weight, a rapid dissolution rate in water, and will form an isotonic solution in water in a concentration of from about 0.5 to about 10 % w/v.

5. The method as defined in claim 4 wherein said carrier material is a water-soluble carrier suitable for intravenous use.

6. The method as defined in claim 5 wherein said carrier material is sorbitol, mannitol, sodium chloride, xylitol or a naturally occurring amino acid.

7. The method as defined in claim 6 wherein said carrier material is sorbitol.

8. The method as defined in claim 4 including the step of dissolving the carrier material in water, mixing the solution of carrier material and the solution of liposomal components, and spray drying the resulting mixture.

9. The method as defined in claim 1 wherein the lipid is a phospholipid.

10. The method as defined in claim 9 wherein the phospholipid is a natural or synthetic lecithin.

11. The method as defined in claim 1 wherein said solution includes a biologically active compound which is a medicament, contrast agent, enzyme, hormone, marker compound or NMR imaging agent.

12. The method as defined in claim 1 wherein the adjuvant is egg phosphatidic acid, dicetyl phosphate, or stearyl amine.

13. The method as defined in claim 1 wherein the adjuvant is a sterol.

14. The method as defined in claim 12 wherein the adjuvant also includes a sterol selected from the group consisting of cholesterol, phytosterol. ergosterol, sitosterol, 7-dehydrocholesterol, and lanosterol.

15. The method as defined in claim 6 wherein the organic solvent is ethanol, methanol, chloroform, dichloromethane, diethyl ether, carbon tetrachloride, ethyl acetate, dioxane or cyclohexane.

16. The method as defined in claim 15 wherein the solvent is methanol, ethanol or chloroform.

17. The method as defined in claim 1 wherein the biologically active compound is amphotericin B.

18. The method as defined in claim 8 wherein the biologically active compound is amphotericin B.

19. The method as defined in claim 18 wherein said carrier material is sorbitol and said adjuvant includes a sterol which is ergosterol.

20. The method as defined in claim 1 wherein said lipid is egg lecithin, soya bean lecithin, dimyristoyl phosphatidyl choline, dipalmitoyl phosphatidyl choline, distearoyl phosphatidyl choline, dioleyl phosphatidyl choline or dilinoleyl phosphatidyl choline.

21. The method as defined in claim 1 wherein the lipid is egg lecithin, the adjuvant is ergosterol, cholesterol or dicetyl phosphate, and the carrier material is sorbitol.

22. The method as defined in claim 1 wherein the srray-drying is carried out at an average temperature within the range of from about 5 to about 60° C.

23. The method as defined in claim 22 wherein the spray-drying is carried out employing from about 300 to about 700 liters of air/hour.

24. A spray-dried mixture of liposomal components which when mixed with water forms a liposome, comprising a dry granular water-soluble free-flowing mixture of liposomal components comprising at least one liposome-forming lipid, optionally, at least one biologically active compound and, optionally, at least one adjuvant which imparts advantgageous properties to the final lipsome and a water-soluble free-flowing physiologically acceptable carrier material, which is suitable for intraveneous injection, which will form an isotonic solution in water in a concentration of from about 0.5 to about 10% w/v, the weight ratio of liposomal components to carrier material being within the range of from about 0.03:1 to about 5:1.

25. The stable liposome precursor as defined in claim 24 including at least one biologically active compound and a carrier material.

26. The stable liposome precursor as defined in claim 25 wherein the biologically active compound is amphotericin B.

27. A spray-dried mixture of liposomal components which when mixed with water forms a liposome, comprising at least one liposome-forming lipid, optionally, at least one biologically active compound, and optionally, at least one adjuvant which imparts advantageous properties to the final liposome, and a physiologically acceptable water-soluble particulate carrier material, suitable for intravenous injection, the weight ratio of liposomal components to carrier material being within the range of from about 0.03:1 to about 5:1, said spray-dried mixture of liposomal components prepared by the method as defined in claim 1.

28. A method for preparing a liposome which comprises mixing the spray-dried mixture of liposomal components as defined in claim 27 with water.

* * * * *